United States Patent
Masuda (10) Patent No.: US 10,070,920 B2
(45) Date of Patent: Sep. 11, 2018

(54) CATHETER

(71) Applicant: Japan Lifeline Co., Ltd., Tokyo (JP)

(72) Inventor: Takuya Masuda, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 0 days.

(21) Appl. No.: 15/507,582

(22) PCT Filed: Jul. 28, 2015

(86) PCT No.: PCT/JP2015/071390
§ 371 (c)(1),
(2) Date: Feb. 28, 2017

(87) PCT Pub. No.: WO2016/113934
PCT Pub. Date: Jul. 21, 2016

(65) Prior Publication Data
US 2017/0281270 A1    Oct. 5, 2017

(30) Foreign Application Priority Data

Jan. 15, 2015    (JP) .................................. 2015-005549

(51) Int. Cl.
*A61N 1/05*        (2006.01)
*A61B 18/14*       (2006.01)
(Continued)

(52) U.S. Cl.
CPC ............ *A61B 18/1492* (2013.01); *A61B 8/12* (2013.01); *A61N 1/0517* (2013.01); *A61B 8/445* (2013.01); *A61M 25/008* (2013.01)

(58) Field of Classification Search
CPC ... A61B 5/0422; A61B 5/0456; A61B 5/6869; A61B 5/6876; A61B 5/042;
(Continued)

(56) References Cited

U.S. PATENT DOCUMENTS 6,033,397 A    3/2000 Laufer et al.
8,224,422 B2   7/2012 Mottola et al.
(Continued)

FOREIGN PATENT DOCUMENTS

JP    11-506947 A    6/1999
JP    2010-12145 A   1/2010
(Continued)

OTHER PUBLICATIONS

Extended European Search Report for European Application No. 15877886.0 dated Oct. 20, 2017.

*Primary Examiner* — Elmer Chao
(74) *Attorney, Agent, or Firm* — Wolf, Greenfield & Sacks, P.C.

(57) ABSTRACT

Provided is a catheter that is manufacturable in a simplified fashion. The catheter 1 includes: a catheter tube 11 including a tip-flexible part 11A that has an inner tube (first tube 61) and a plurality of divided tube members 620 to 625 that are disposed on outer circumference of the inner tube and independent of each other; one or a plurality of metal rings disposed in the tip-flexible part 11A; one or a plurality of temperature sensors disposed corresponding to the one or the plurality of metal rings; and a handle 12 attached at a base end of the catheter tube 11. A rate of a thickness of the metal ring to an outer diameter of the metal ring is 7.5% or greater. The metal ring and the plurality of divided tube members 621 to 625 are both so disposed in the tip-flexible part 11A as to be fitted on an outer circumferential surface of the inner tube side by side in an axial direction of the catheter tube 11.

6 Claims, 9 Drawing Sheets

(51) Int. Cl.
*A61B 8/12* (2006.01)
*A61M 25/00* (2006.01)
*A61B 8/00* (2006.01)

(58) Field of Classification Search
CPC ............ A61B 5/6852; A61B 2562/222; A61B 2562/12; A61B 2562/0209; A61N 1/0563; A61N 1/056; B32B 38/0012; B32B 37/142; B32B 2457/00; B32B 2535/00; A61M 25/0012; A61M 25/0013
See application file for complete search history.

(56) References Cited

U.S. PATENT DOCUMENTS

| | | |
|---|---|---|
| 2007/0021741 A1 | 1/2007 | Abboud et al. |
| 2007/0106289 A1* | 5/2007 | O'Sullivan ........ A61B 18/1492 606/41 |
| 2009/0149848 A1 | 6/2009 | Werneth et al. |
| 2011/0319948 A1* | 12/2011 | Onodera ............. A61B 5/0422 607/5 |
| 2012/0035603 A1 | 2/2012 | Lenihan |
| 2012/0089123 A1 | 4/2012 | Organ et al. |
| 2013/0012940 A1 | 1/2013 | Desinger et al. |

FOREIGN PATENT DOCUMENTS

| | | |
|---|---|---|
| JP | 2010505592 A | 2/2010 |
| JP | 2012515612 A | 7/2012 |
| JP | 2014-508547 A | 4/2014 |

\* cited by examiner

[FIG. 9]
COMPARATIVE EXAMPLE

CATHETER

RELATED APPLICATIONS

This Application is a National Stage of PCT/JP2015/071390 filed on Jul. 28, 2105 which claims Foreign priority benefits under 35 U.S.C. § 119(a)-(d) or 35 U.S.C. § 365(b) of Japanese application number 2015-005549, filed Jan. 15, 2015.

TECHNICAL FIELD

The invention relates to a catheter having a temperature sensor.

BACKGROUND ART

An operation that performs cauterization or "ablation" with use of an ablation catheter has been performed as one of medical treatments for arrhythmia, etc. Such ablation that uses the ablation catheter may be performed on a site that involves the arrhythmia inside the heart, for example. In general, methods of the ablation may be roughly classified into a method that performs heating and a method that performs cooling. More specifically, the methods of the ablation may be roughly classified into a high-temperature ablation that uses a high frequency current and a low-temperature ablation that uses liquid nitrous oxide, liquid nitrogen, etc. When performing the ablation of a site such as the posterior wall of the left atrium of the heart by means of the ablation catheter, i.e., upon surgical ablation of the left atrium, the esophagus located in the vicinity of the posterior wall of the left atrium may typically be heated or cooled as well, leading to a possible damage of the esophagus.

To address this, a method has been proposed that measures or monitors information on a temperature in the esophagus, such as a temperature of the medial wall of the esophagus. The method involves insertion of a temperature measuring catheter or a so-called "esophageal catheter" into the esophagus through the nose of a patient by means of a transnasal approach. For example, reference is made to Patent Literatures 1 and 2. The temperature measuring catheter includes a temperature sensor in the vicinity of a metal ring located near a tip of a catheter tube. The temperature sensor measures a temperature in the esophagus. A system that achieves such a method, or a "catheter system", includes the foregoing temperature measuring catheter and a temperature measuring apparatus that measures the temperature in the esophagus by means of the temperature sensor of the temperature measuring catheter.

Monitoring the temperature in the esophagus in such a manner makes it possible to avoid the possible damage of the esophagus upon, for example, the foregoing surgical ablation of the left atrium.

CITATION LIST

Patent Literature

Patent Literature 1: Japanese Unexamined Patent Application Publication (Translation of PCT Application) No. 2010-505592

Patent Literature 2: Japanese Unexamined Patent Application Publication (Translation of PCT Application) No. 2012-515612

SUMMARY OF INVENTION

In general, it is required that a temperature measuring catheter be manufacturable in a simplified fashion or easily. What is therefore desired is a proposal of a method that makes the temperature measuring catheter manufacturable in a simplified fashion.

The invention has been made in view of such a circumstance, and it is an object of the invention to provide a catheter that is manufacturable in a simplified fashion.

A catheter according to the invention includes: a catheter tube including a tip-flexible part that has an inner tube and a plurality of divided tube members that are disposed on outer circumference of the inner tube and independent of each other; one or a plurality of metal rings disposed in the tip-flexible part; one or a plurality of temperature sensors disposed corresponding to the one or the plurality of metal rings; and a handle attached at a base end of the catheter tube. A rate of a thickness of the metal ring to an outer diameter of the metal ring, i.e., the thickness of the metal ring/the outer diameter of the metal ring, is 7.5% or greater. The metal ring and the plurality of divided tube members are both so disposed in the tip-flexible part as to be fitted on an outer circumferential surface of the inner tube side by side in an axial direction of the catheter tube. For example, the outer diameter of the metal ring may be in a range from 1.3 mm to 4.0 mm, and the thickness of the metal ring may be in a range from 0.15 mm to 0.50 mm, for example.

In the catheter according to the invention, the metal ring has the thick structure. In other words, the rate is 7.5% or greater. Thus, a rate at which heat having transferred to the metal ring dissipates to the surrounding tissues becomes smaller than a metal ring having a thin structure. Hence, upon measuring an internal temperature of, for example, a hollow organ inside the body, such as the esophagus, by means of the temperature sensor, the internal temperature of the hollow organ having been subjected to heating or cooling is transmitted accurately to the temperature sensor. As a result, an accuracy of measurement upon measuring the internal temperature increases as compared with the metal ring having the thin structure. However, upon forming the tip-flexible part of the catheter tube, such a thick-structured metal ring may involve difficulties in employing an example method that causes the metal ring to be embedded into the outer circumferential surface of a second tube by striking the metal ring from outside. To address this, in the catheter according to the invention, the one or the plurality of metal rings each provided corresponding to the temperature sensor and the plurality of divided tube members that are independent of each other are both so disposed in the tip-flexible part as to be fitted on the outer circumferential surface of the inner tube side by side in the axial direction of the catheter tube. This makes it easier to form the tip-flexible part even when the metal ring is made thick as described above.

In the catheter according to the invention, desirably, the inner tube may have an opening that is formed in the axial direction from a tip end of the inner tube and allows the metal ring and the temperature sensor to be electrically coupled to each other. This facilitates the electrical coupling of the metal ring and the temperature sensor, making it easier to so dispose the metal ring as to be fitted on the outer circumferential surface of the inner tube. This also facilitates the formation of the opening on the inner tube, making it even easier to form the tip-flexible part.

In the catheter according to the invention, desirably, the metal ring and the plurality of divided tube members each may include an outer circumferential surface that has a flat shape in the axial direction in the tip-flexible part. This achieves the following example advantages as compared with an example case in which either of those outer circumferential surfaces is formed in a non-flat shape, such as a case in which either of those outer circumferential surfaces has a bulged shape, for example. An advantage is that a risk of damaging, for example, the inside of the nasal cavity or the hollow organ is suppressed, making it possible to reduce a burden imposed on a patient. Another advantage is that the metal ring comes into surface contact with, for example, the medial wall of the hollow organ, making it possible to increase responsiveness to a change in the temperature upon measuring the internal temperature and thereby to increase an accuracy of the measurement as compared with the example case in which the metal ring has the non-flat shape and thus comes into point contact with the medial wall of the hollow organ. Yet another advantage is that forming the outer circumferential surface into the flat shape in the axial direction makes it possible to decrease a diameter of the catheter tube, i.e., the tip-flexible part.

The catheter according to the invention may desirably further include a deflection mechanism that includes the handle and deflects the tip-flexible part. This allows for insertion of the catheter tube while varying a shape of a region near a tip, i.e., the tip-flexible part, of the catheter tube. Hence, it is possible to make the catheter tube pass through, for example, the complex-structured nasal cavity smoothly and insert the catheter tube to the esophagus easily.

According to the catheter of the invention, the metal ring and the plurality of divided tube members are both so disposed in the tip-flexible part of the catheter tube as to be fitted on the outer circumferential surface of the inner tube side by side in the axial direction of the catheter tube. Thus, it is possible to make the tip-flexible part easily formable even when the metal ring is made thick. Hence, it is possible to make the catheter manufacturable in a simplified fashion.

DESCRIPTION OF EMBODIMENTS

Some embodiments of the invention are described in detail below, in the following order, with reference to drawings.
1. Embodiment (an example in which a plurality of sets of thick-structured metal rings and temperature sensors are provided)
2. Modification Examples
[Embodiment]
[Example of Outline Configuration]

Figure 1:
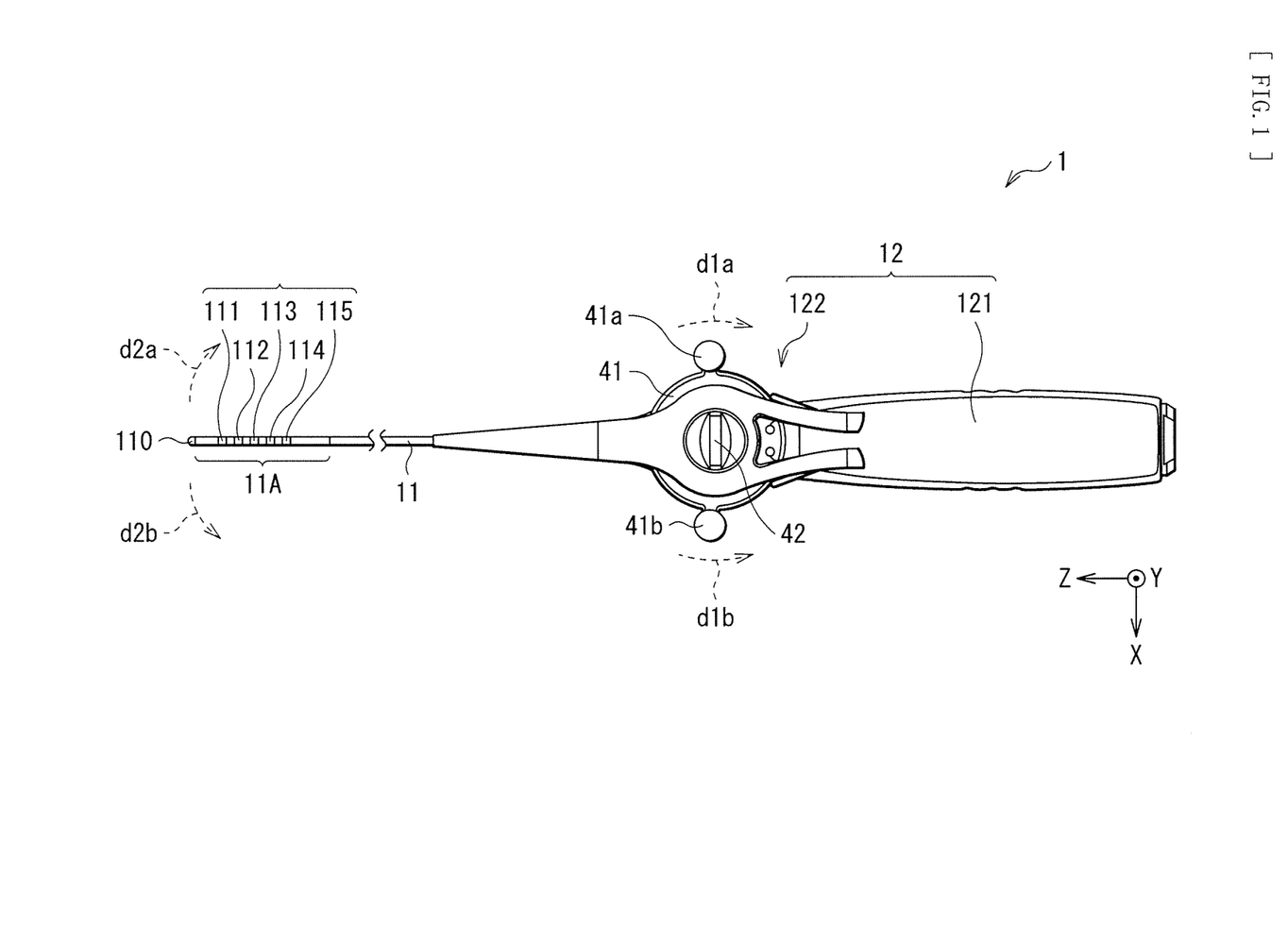
FIG. 1 schematically illustrates an example of an outline configuration of a catheter according to an embodiment of the invention.

FIG. 1 schematically illustrates an example of an outline configuration, on a Z-X plane, of a catheter referred to as a "catheter 1" according to an embodiment of the invention. The catheter 1 may be a catheter or a so-called "esophageal catheter" used for measurement of information on an internal temperature of a hollow organ inside the body of a patient upon performing a medical treatment of, for example, arrhythmia of the patient, e.g., upon performing surgical ablation of the left atrium. For example, the hollow organ may be the esophagus. The internal temperature may be a temperature of the medial wall of the hollow organ. More specifically, the catheter 1 may be inserted into the esophagus, or any other part, of the patient through the nose by means of a transnasal approach, as described later in greater detail.

Referring to FIG. 1, the catheter 1 includes a catheter tube 11 or a "catheter shaft", and a handle 12 attached at a base end of the catheter tube 11. The catheter tube 11 may serve as a catheter body or an "elongated part".

[Catheter Tube 11]

The catheter tube 11 may have a tubular structure having flexibility, and has a shape that extends in a direction of its own axis, i.e., in a Z-axis direction. In other words, the catheter tube 11 may have a hollow tube-shaped member. More specifically, a length in the axial direction of the catheter tube 11 may be about several times to about several ten times as long as a length in an axial direction, i.e., in the Z-axis direction, of the handle 12. The catheter tube 11 may be configured by a tube having the same property in the axial direction thereof. It is, however, preferable that the catheter tube 11 have a tip end part and a base end part as described in this embodiment. The tip end part, or a "tip-flexible part 11A", may have a relatively superior flexibility. The base end part may be formed integrally with the tip end part in the axial direction, and has a relatively higher rigidity than that of the tip end part.

The catheter tube 11 may also have a so-called single lumen structure in which a single lumen is so formed therein as to extend in the axial direction thereof, or a so-called multi-lumen structure in which a plurality of lumens, such as four lumens, are formed therein. The lumen may encompass an inner hole, a pore, or a through hole. Alternatively, the catheter tube 11 may include therein both a region having the single lumen structure and a region having the multi-lumen structure. Such a lumen provided in the catheter tube 11 may include various fine wires that are inserted therethrough while they are electrically insulated from one another. Examples of the various fine wires may include a pair of operating wires 40a and 40b and conduction wires L1 to L5 both of which are to be described later.

The pair of operating wires 40a and 40b, or "tension wires", among the various fine wires each may extend through the inside of the catheter tube 11 to be led to the inside of the handle 12. The pair of operating wires 40a and 40b may be used upon a deflection operation of the later-described tip end part, or the "tip-flexible part 11A", of the catheter tube 11. In other words, the operating wires 40a and 40b each may be used to deflect a region near a tip of the catheter tube 11 as exemplified by arrows d2a and d2b of FIG. 1. The operating wires 40a and 40b each may have a tip end fixed around a tip inside the catheter tube 11 by means of, for example, an anchor and a solder. The operating wires 40a and 40b each may also have a base end that extends from the inside of the catheter tube 11 to the inside of the handle 12 as described above and fixed by an unillustrated fastener inside the handle 12. The operating wires 40a and 40b each may be made of stainless steel (SUS) or a super-elastic metal material such as nickel titanium (NiTi), and each may have a diameter in a range from about 100 μm to about 500 μm. More specifically, the operating wires 40a and 40b each may have a diameter of 200 μm, for example. However, it is not strictly necessary for each of the operating wires 40a and 40b to be made of a metal material. For example, the operating wires 40a and 40b each may be a high-strength non-conductive wire or other suitable wire.

The catheter tube 11 may be made of a synthetic resin such as polyolefin, polyamide, polyetherpolyamide, polyurethane, nylon, and polyether blockamide. The length in the axial direction of the catheter tube 11 may preferably be in a range from about 500 mm to about 1200 mm, and may be 800 mm according to a preferred example. The tip-flexible part 11A of the catheter tube 11 may have a length in the axial direction which may preferably be in a range from 40 mm to 100 mm, and more preferably be in a range from 50 mm to 80 mm. An outer diameter, i.e., an outer diameter in X-Y cross section, of the catheter tube 11 may be in a range from 1.3 mm to 4.0 mm, and may be 2.4 mm according to a preferred example.

Further, one or a plurality of metal rings, such as five metal rings 111 to 115 in this embodiment, and one tip 110 are disposed at a predetermined interval near the tip (i.e., the tip-flexible part 11A) of the catheter tube 11 as illustrated in FIG. 1. More specifically, the metal rings 111 to 115 serving as temperature measuring metal rings each may be fixedly disposed at a mid-part of the tip-flexible part 11A, i.e., around a middle region of the tip-flexible part 11A, whereas the tip 110 may be fixedly disposed at a most distal end of the tip-flexible part 11A.

Note that an example of a detailed configuration of the tip-flexible part 11A of the catheter tube 11 is described later with reference to FIGS. 2 to 6.

[Handle 12]

The handle 12 illustrated in FIG. 1 may be a part where an operator such as a doctor grabs or holds upon using the catheter 1. The handle 12 may have a handle body 121 and a rotary operation part 122 as illustrated in FIG. 1. The handle body 121 may be attached at the base end of the catheter tube 11.

The handle body 121 may be equivalent to a part or a "grip" where the operator actually holds, and may have a shape that extends in an axial direction, i.e., the Z-axis direction, of the handle body 121. The handle body 121 may be made of a synthetic resin such as polycarbonate and acrylonitrile butadiene styrene copolymer (ABS).

The rotary operation part 122 may be a part used upon performing the deflection operation that deflects the region near the tip of the catheter tube 11 in conjunction with the previously-described pair of operating wires 40a and 40b, as described later in greater detail. The region near the tip of the catheter tube 11 is, in other words, the tip-flexible part 11A. More specifically, the rotary operation part 122 is operated or subjected to a "rotary operation" upon performing such a deflection operation. This means that, in this embodiment, the handle 12, i.e., the rotary operation part 122, and the pair of operating wires 40a and 40b correspond to a specific example of a "deflection mechanism" according to the invention. The rotary operation part 122 may include a rotary plate 41 and an adjustment knob 42 as illustrated in FIG. 1.

The rotary plate 41 may be a member rotatably attached to the handle body 121 around a rotation axis that is perpendicular to a longitudinal direction, i.e., the Z-axis direction, of the handle body 121. The rotation axis, in other words, corresponds to a Y-axis direction. The rotary plate 41 may be equivalent to a part actually operated by the operator upon the previously-described rotary operation, and may have a substantially disk-like shape. More specifically, in this embodiment, an operation is made possible in which the rotary plate 41 is rotated in two ways in the Z-X plane relative to the handle body 121 as denoted by arrows d1a and d1b in FIG. 1. In other words, a rotary operation of the rotary plate 41 is made possible around the rotation axis.

The rotary plate 41 may be integrally provided with a pair of knobs 41a and 41b that are located on a side surface of the rotary plate 41. In this embodiment, the knob 41a and the knob 41b may be disposed at their respective positions that are symmetric with respect to a point around the rotation axis of the rotary plate 41 as illustrated in FIG. 1. The knobs 41a and 41b each may be equivalent to a part operated or pushed by, for example, fingers of one hand when the operator performs the rotary operation of the rotary plate 41. For example, the rotary plate 41 may be made of a material similar to the previously-described material of the handle body 121, such as a synthetic resin.

The adjustment knob 42 may be a member that is rotatable in the Z-X plane, and fixes or keeps a position at which the rotary plate 41 is rotated. In other words, the adjustment knob 42 may fix or keep a state in which the region near the tip of the catheter tube 11 is curved. More specifically, the operator may twist the adjustment knob 42 to fix the rotary plate 41 to the handle body 121. This allows for fixation of the position at which the rotary plate 41 is rotated.

[Example of Detailed Configuration of Tip-Flexible Part 11A]

A description is given next, with reference to FIGS. 2 to 6, of an example of a detailed configuration of the tip-flexible part 11A of the catheter tube 11.

Figure 2:
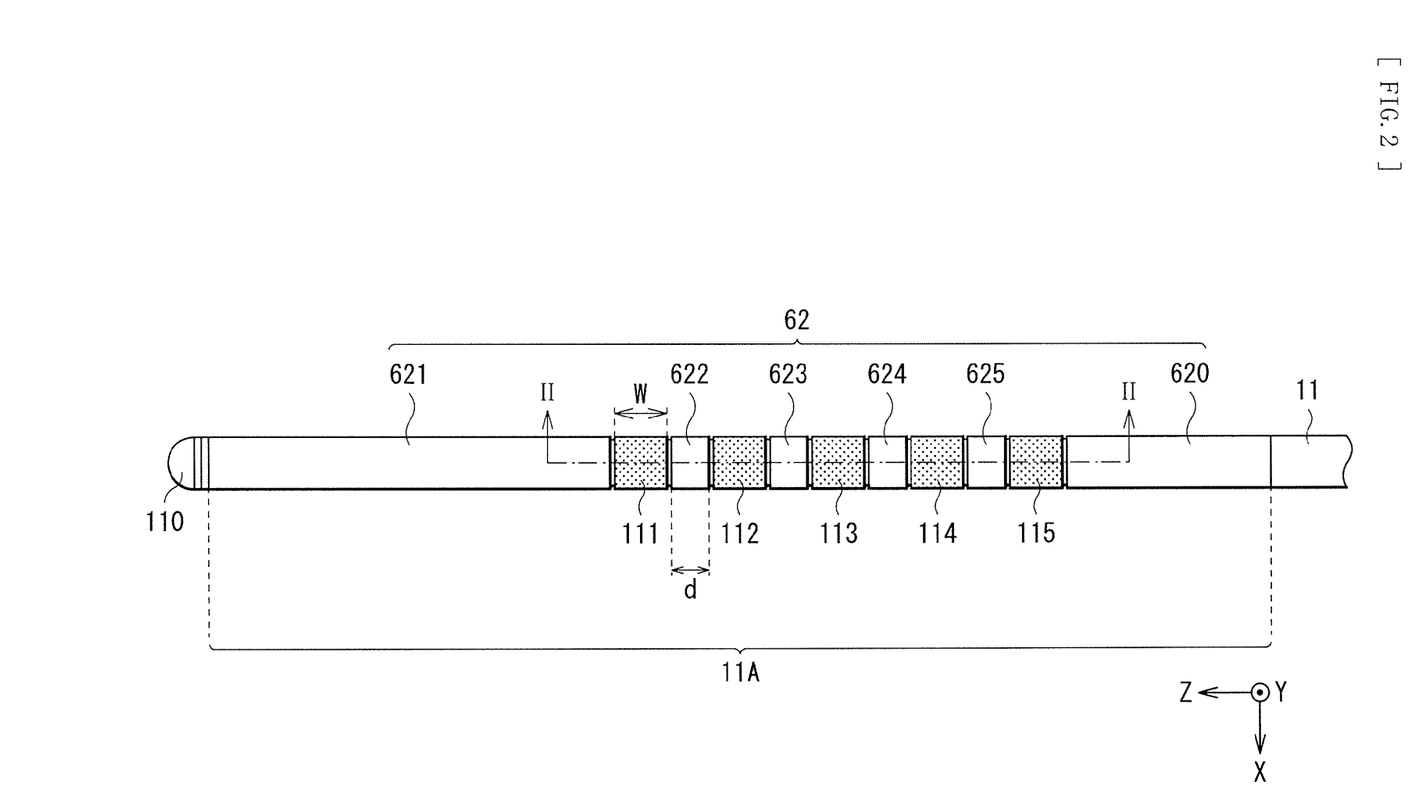
FIG. 2 schematically illustrates an example of a detailed configuration of a tip-flexible part of a catheter tube illustrated in FIG. 1.
Figure 3:
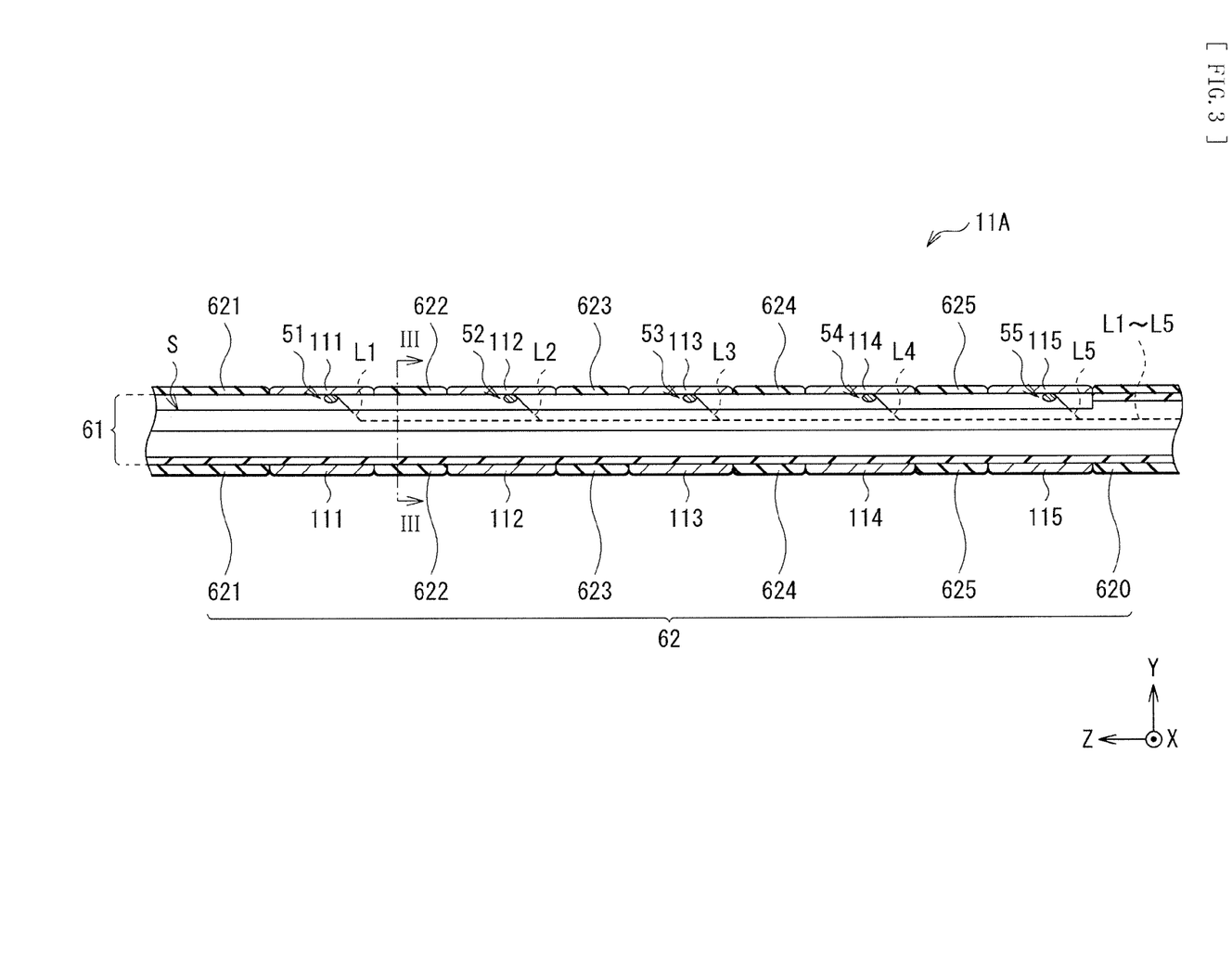
FIG. 3 schematically illustrates an example of a cross-sectional configuration of the tip-flexible part illustrated in FIG. 2.
Figure 4:
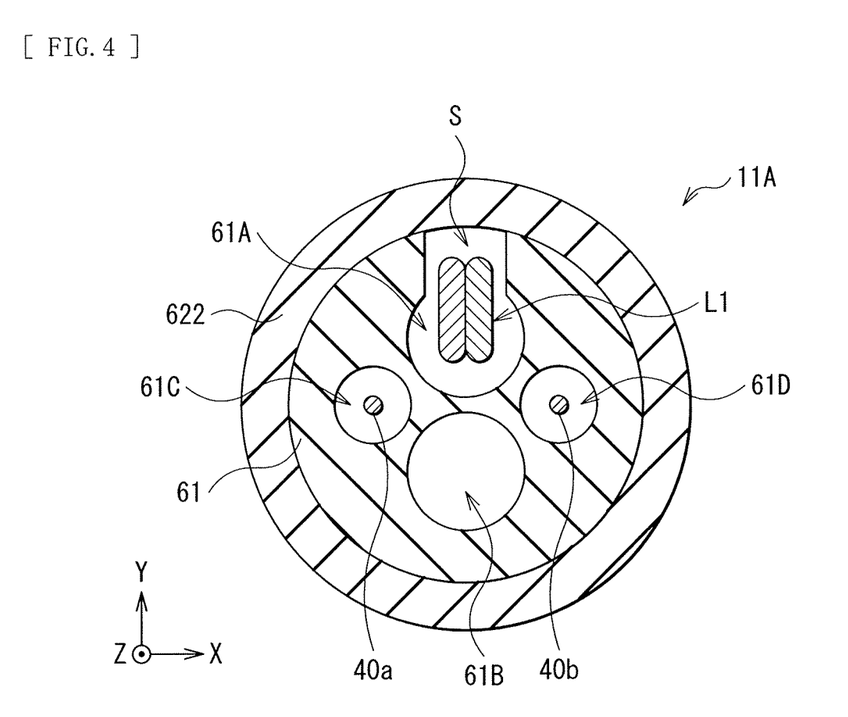
FIG. 4 schematically illustrates an example of the cross-sectional configuration of the tip-flexible part illustrated in FIG. 3 as viewed in another direction.
Figure 5:
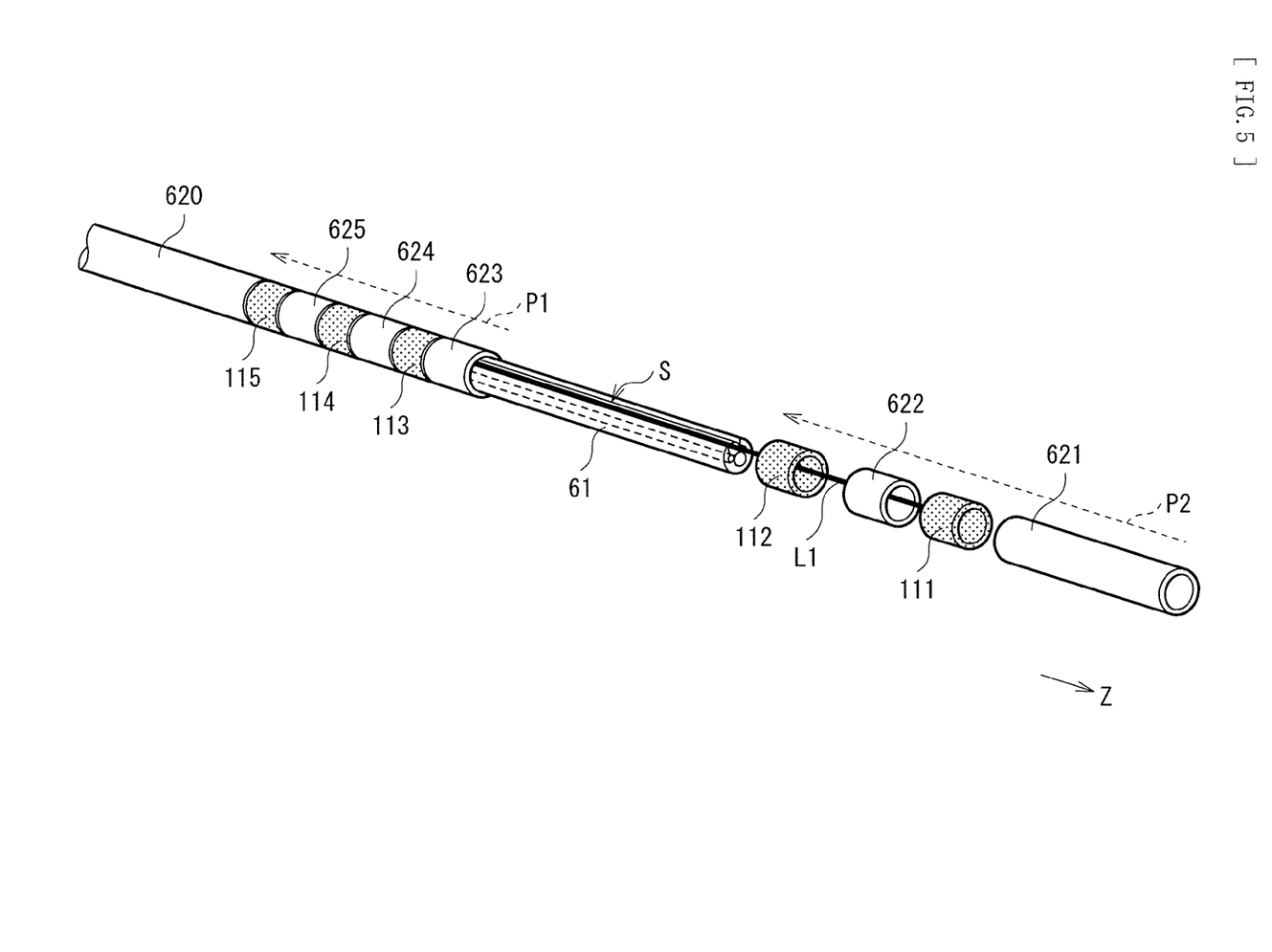
FIG. 5 is a schematic exploded perspective view of the configuration example of the tip-flexible part illustrated in each of FIGS. 2 to 4.
Figure 6:
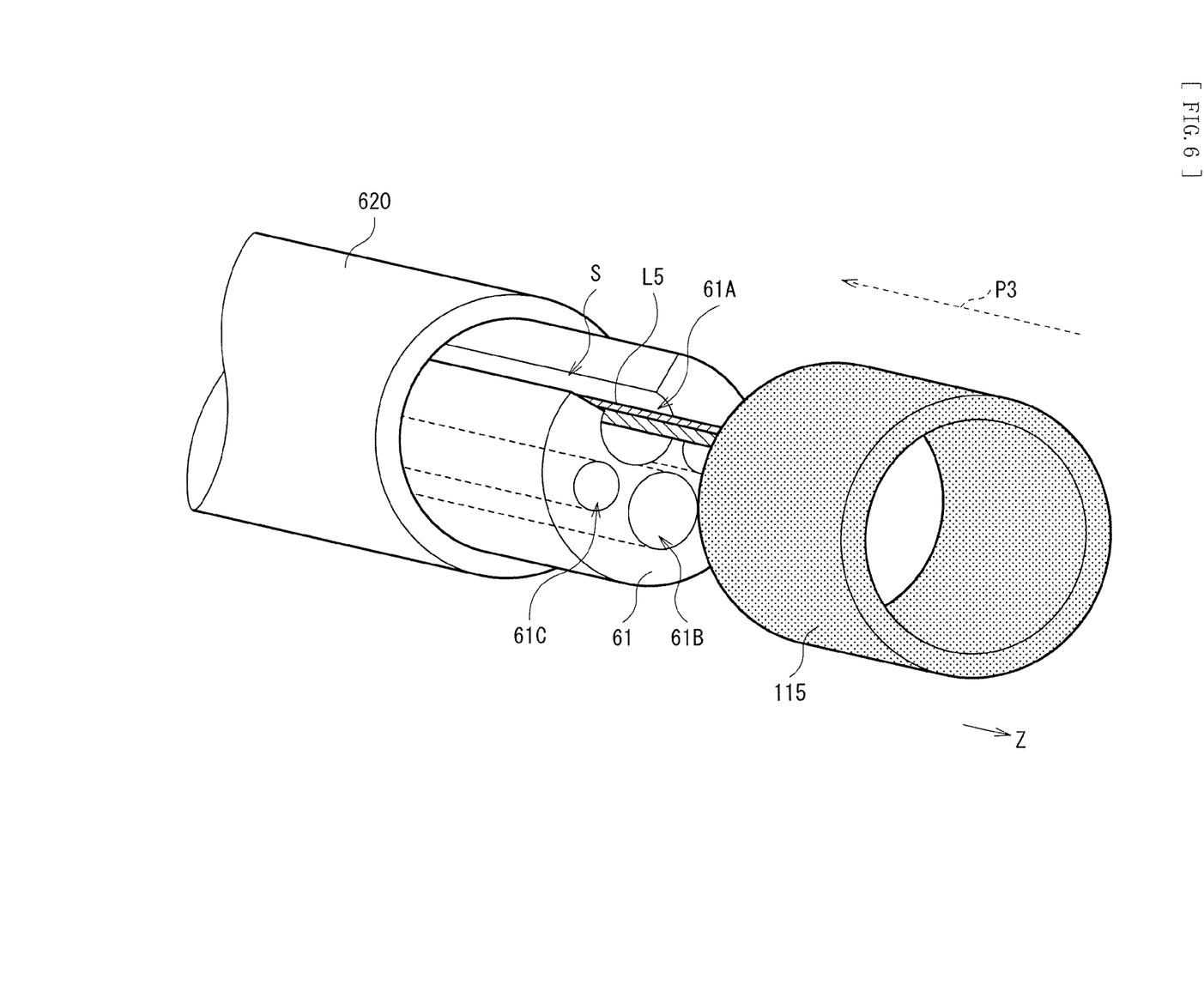
FIG. 6 is a schematic exploded perspective view of a part of the tip-flexible part illustrated in FIG. 5 in an enlarged fashion.

FIG. 2 schematically illustrates one example of the detailed configuration, on the Z-X plane, of the tip-flexible part 11A of the catheter tube 11 illustrated in FIG. 1. FIG. 3 schematically illustrates an example of a cross section of the tip-flexible part 11A illustrated in FIG. 2, i.e., illustrates an example of a Y-Z cross-sectional configuration, taken along line II-II and seen in the direction of arrows of FIG. 2. FIG. 4 schematically illustrates an example of the cross section of the tip-flexible part 11A illustrated in FIG. 3, i.e., illustrates an example of an X-Y cross-sectional configuration, taken along line and seen in the direction of arrows of FIG. 3. FIG. 5 is a schematic exploded perspective view of the configuration example of the tip-flexible part 11A illustrated in each of FIGS. 2 to 4. FIG. 6 is a schematic exploded perspective view of a part of the tip-flexible part 11A illustrated in FIG. 5 in an enlarged fashion. Note that illustration of a part of the tip-flexible part 11A is omitted in FIG. 6 for simplified illustration.

[First Tube 61 and Second Tube 62]

Referring to FIGS. 2 to 6, the tip-flexible part 11A of the catheter tube 11 may have a multilayer structure, i.e., a two-layer structure, that includes a first tube 61 and a second tube 62. The first tube 61 serving as an inner tube may be disposed on inner circumference side of the tip-flexible part 11A, whereas the second tube 62 serving as an outer tube may be disposed on outer circumference side of the first tube 61. In this embodiment, the first tube 61 and the second tube 62 may be tubes or "tubular structures" that are separated from each other. Further, the second tube 62 is configured by a plurality of divided tube members that are independent from each other. In this embodiment, the plurality of divided tube members may include six divided tube members 620, 621, 622, 623, 624, and 625.

The first tube 61 may have the multi-lumen structure having four lumens 61A, 61B, 61C, and 61D that are formed therein in this embodiment as illustrated in FIGS. 4 and 6. More specifically, in this embodiment, the two lumens 61A and 61B may be disposed side by side in the Y-axis direction inside the second tube 62, and the two lumens 61C and 61D may be disposed side by side in the X-axis direction inside the second tube 62. The lumens 61A and 61B each may have a relatively large diameter, whereas the lumens 61C and 61D each may have a relatively small diameter. Further, in this embodiment, conduction wires, i.e., the conduction wires L1 to L5, of respective temperature sensors to be described later may be inserted through the lumen 61A, whereas the previously-described operating wires 40a and 40b may be inserted respectively through the lumens 61C and 61D in an individual fashion.

The first tube 61 and the second tube 62, including the divided tube members 620 to 625, each may be made of, for example, the previously-described synthetic resin. For example, the first tube 61 and the second tube 62 each may be made of a material such as polyolefin, polyamide, polyetherpolyamide, polyurethane, nylon, and polyether blockamide.

The first tube 61 may have an outer diameter, i.e., an outer diameter in X-Y cross section, that may preferably be in a range from 1.0 mm to 3.0 mm, and that may be 1.95 mm according to a preferred example.

The second tube 62, or each of the divided tube members 620 to 625, may similarly have an outer diameter that may preferably be in a range from 1.3 mm to 4.0 mm, and that may be 2.4 mm according to a preferred example. The second tube 62, or each of the divided tube members 620 to 625, may have an inner diameter that may preferably be in a range from 1.0 mm to 3.0 mm, and that may be 1.95 mm according to a preferred example. Further, the divided tube members 621 to 625 each may have a length in an axial direction, i.e., in the Z-axis direction, that may be in a range from 1.0 mm to 20.0 mm, for example, and that may be 5.0 mm according to a preferred example.

[Metal Rings 111 to 115 and Tip 110]

As already described with reference to FIG. 1, the tip-flexible part 11A may be disposed with the five metal rings 111 to 115 and one tip 110 as illustrated in FIG. 2. The tip 110 may be fixedly disposed at the most distal end of the tip-flexible part 11A. The five metal rings 111 to 115 may be disposed side by side in this order at a predetermined interval from the tip end, i.e., from the tip 110, to a base end of the tip-flexible part 11A. The predetermined interval is, in other words, a metal-ring-to-metal-ring distance "d" illustrated in FIG. 2. The metal-ring-to-metal-ring distance d may preferably be 5 mm or less, for example, and more preferably be in a range from about 2 mm to about 4 mm.

According to one example, the metal-ring-to-metal-ring distance d may be 2 mm. Further, the metal rings 111 to 115 each may have a metal ring width "w" illustrated in FIG. 2 which may preferably be 5 mm or less, for example, and more preferably be in a range from about one mm to about 4 mm. According to one example, the metal ring width w may be 2 mm.

The metal rings 111 to 115 in this embodiment each may also have an outer diameter and an inner diameter that are about the same as those of the foregoing second tube 62, i.e., those of each of the divided tube members 620 to 625. More specifically, the outer diameter of each of the metal rings 111 to 115 may preferably be in a range from 1.3 mm to 4.0 mm, and may be 2.4 mm according to a preferred example. The inner diameter of each of the metal rings 111 to 115 may preferably be in a range from 1.0 mm to 3.0 mm, and may be 1.95 mm according to a preferred example. Further, the metal rings 111 to 115 each have a thick structure that may have a thickness typically in a range from 0.15 mm to 0.50 mm. Here, the metal rings 111 to 115 each may have a thickness that may preferably be in a range from 0.20 mm to 0.50 mm, and that may be 0.225 mm according to a preferred example. This means that the thickness of each of the metal rings 111 to 115 may be about 2 times to about 10 times as large as a thickness of an existing thin-structured metal ring typically in a range from about 0.05 mm to about 0.07 mm, for example.

Note that making the outer diameter of each of the metal rings 111 to 115 less than 1.3 mm requires each member structuring the catheter 1, including the metal rings 111 to 115 as well, to be extremely small. This may cause an assembly work to be difficult, which may in turn lead to difficulties in manufacturing. This may also result in possible occurrence of a product defect, such as disconnection of the fine wires such as the operating wires 40a and 40b and the conduction wires L1 to L5. Making the outer diameter of each of the metal rings 111 to 115 greater than 4.0 mm makes the catheter tube 11 difficult to pass through the nasal cavity smoothly.

Here, a proportion of the thick structure of each of the metal rings 111 to 115 to the outer diameter of each of the metal rings 111 to 115 may be equal to or greater than 15%. The proportion is, in other words, "thickness structure/outer diameter of each of the metal rings 111 to 115". In this embodiment, the outer diameter of each of the metal rings 111 to 115 may be substantially equal to the outer diameter of the tip-flexible part 11A of the catheter tube 11. The thick structure of each of the metal rings 111 to 115 is defined as one thickness and another thickness (thickness×2) of each of the metal rings 111 to 115. In contrast, the proportion of the existing thin-structured metal ring having the typical thickness as described above is less than 10%.

In other words, for example, a rate of the thickness of each of the metal rings 111 to 115 to the outer diameter of each of the metal rings 111 to 115 is typically 7.5% or greater, may preferably be equal to or greater than 8.0%, and may more preferably be equal to or greater than 9.0%. According to a preferred example, the rate may be 9.4% (=0.225/2.4). The rate is, in other words, "thickness of each of the metal rings 111 to 115/outer diameter of each of the metal rings 111 to 115". In this embodiment, the outer diameter of each of the metal rings 111 to 115 may be substantially equal to the outer diameter of the tip-flexible part 11A of the catheter tube 11. In contrast, the rate of the existing thin-structured metal ring having the typical thickness as described above is less than 5.0%.

Note that making the rate 7.5% or greater makes it possible to measure the internal temperature of a site such as esophagus E at a favorable accuracy. However, making the rate less than 7.5% leads to a large variation in temperature to be detected, depending on which part of, for example, the esophagus E the connection parts are located. This in turn prevents the measurement of the internal temperature of, for example, the esophagus E from being performed at a favorable accuracy. The connection parts are each a part at which the later-described temperature sensor, including temperature sensors 51 to 55, and corresponding one of the metal rings 111 to 115 are coupled together.

The metal rings 111 to 115 each may be made of a metal material having a favorable electrical conductivity, such as aluminum (Al), copper (Cu), stainless steel (SUS), gold (Au), and platinum (Pt). The tip 110 may also be made of a metal material similar to that of each of the metal rings 111 to 115, for example. Alternatively, the tip 110 may be made of a resin material such as a silicone rubber resin and polyurethane.

[Temperature Sensors 51 to 55]

The tip-flexible part 11A of the catheter tube 11 is provided therein with five temperature sensors 51 to 55 that are respectively disposed near the metal rings 111 to 115 and disposed corresponding to the metal rings 111 to 115, respectively, as schematically illustrated in FIG. 3. For example, the temperature sensors 51 to 55 may be disposed at respective positions at which the temperature sensors 51 to 55 respectively face the metal rings 111 to 115. More specifically, in this embodiment, a plurality of sets of metal rings 111 to 115 and temperature sensors 51 to 55, i.e., five sets configured by the five metal rings 111 to 115 and the five temperature sensors 51 to 55, are provided in a one-to-one correspondence relationship. Note that no temperature sensor that forms a pair with, or is electrically coupled to, the tip 110 may be provided near the tip 110 in this embodiment.

The temperature sensors 51 to 55 each may serve as a sensor that measures the internal temperature of a site such as the esophagus upon, for example, the surgical ablation of the left atrium. The temperature sensors 51 to 55 may be electrically coupled to the metal rings 111 to 115 in an individual fashion, respectively. More specifically, the temperature sensor 51 may be embedded near the metal ring 111, and may be electrically coupled to the metal ring 111 as illustrated in FIG. 3. Similarly, the temperature sensor 52 may be embedded near the metal ring 112, and may be electrically coupled to the metal ring 112. The temperature sensor 53 may be embedded near the metal ring 113, and may be electrically coupled to the metal ring 113. The temperature sensor 54 may be embedded near the metal ring 114, and may be electrically coupled to the metal ring 114. The temperature sensor 55 may be embedded near the metal ring 115, and may be electrically coupled to the metal ring 115. For example, such electrical coupling may be achieved by an individual spot welding of the temperature sensors 51 to 55 onto corresponding inner circumferential surfaces of the respective metal rings 111 to 115.

The temperature sensors 51 to 55 each may have a configuration in which a thermocouple is used, for example. In other words, the temperature sensors 51 to 55 each may utilize a temperature measuring junction by means of the thermocouple. Further, the conduction wires L1 to L5 serving as leads may be electrically coupled to the temperature sensors 51 to 55 in an individual fashion, respectively, and may include metal wires as illustrated in FIGS. 3 to 6. The metal wires are different in kind from each other and structure the thermocouple. The conduction wires L1 to L5 each may be inserted through the lumen provided in the catheter tube 11 and led to the inside of the handle 12 as described previously. In this embodiment, the conduction wires L1 to L5 each may be inserted through the lumen 61A as described previously with reference to FIG. 4.

The first tube 61 of the tip-flexible part 11A may have an opening S as illustrated by ways of example in FIGS. 3 to 6. The opening S may encompass a side hole or a through hole, and allow for the individual electrical coupling of the temperature sensors 51 to 55 and the metal rings 111 to 115. More specifically, the temperature sensors 51 to 55 may be welded onto the corresponding inner circumferential surfaces of the respective metal rings 111 to 115 by means of the individual spot welding as described above through the opening S.

The opening S may be formed at least in a region, of the first tube 61, in which the metal rings 111 to 115 are disposed as illustrated by way of example in FIGS. 3 to 6. In other words, the opening S may be formed only in regions in which the respective metal rings 111 to 115 are disposed, or may be formed also in a region in which the divided tube members 620 to 625 are disposed as in this embodiment as illustrated by way of example in FIG. 5. More specifically, in this embodiment, the opening S may be formed in the axial direction, i.e., the Z-axis direction, of the tip-flexible part 11A in a shape of a slit as illustrated in FIG. 5. In other words, the opening S may be formed in a single, continuous rectangular shape.

[Example of Detailed Configuration of Each Member]

As illustrated by way of example in FIGS. 2, 3, and 5, the five metal rings 111 to 115 and the five divided tube members 621 to 625 are both so disposed in the tip-flexible part 11A as to be fitted on an outer circumferential surface of the first tube 61 side by side in the axial direction, i.e., the Z-axis direction, of the catheter tube 11. The term "fit" encompasses the term "place" and "mount". More specifically, in this embodiment, the five metal rings 111 to 115 are so disposed as to be fitted side by side in the axial direction of the catheter tube 11 with the four divided tube members 622, 623, 624, and 625 interposed in between. In other words, in this embodiment, the metal rings and the divided tube members may be disposed alternately from the tip end of the tip-flexible part 11A, i.e., from the tip 110, to the base end of the tip-flexible part 11A in order of the divided tube member 621, the metal ring 111, the divided tube member 622, the metal ring 112, the divided tube member 623, the metal ring 113, the divided tube member 624, the metal ring 114, the divided tube member 625, the metal ring 115, and the divided tube member 620.

As described later in greater detail with reference to FIGS. 7A to 7C, such a side-by-side arrangement structure may be formed in the following example manner as denoted, for example, by arrows P1 and P2 of FIG. 5 and an arrow P3 of FIG. 6. Namely, the metal rings 111 to 115 and the divided tube members 621 to 625, excluding the divided tube member 620, may be fitted on the outer circumferential surface of the first tube 61 sequentially in the axial direction, i.e., the Z-axis direction, of the tip-flexible part 11A such that the foregoing side-by-side arrangement structure is formed.

Further, in the tip-flexible part 11A, outer circumferential surfaces of the respective metal rings 111 to 115 and outer circumferential surfaces of the respective divided tube members 620 to 625 each may form a flat shape or a substantially flat shape in the axial direction, i.e., the Z-axis direction, of the tip-flexible part 11A as illustrated by way of example in FIGS. 2, 3, and 5. In other words, the metal rings 111 to 115 and the divided tube members 620 to 625 each may have the outer circumferential surface that is free from, for example, a protrusion, a step, or any other shape and thus they may form a smooth outer circumferential surface as if the tip-flexible part 11A has a single tube structure at first glance. It is to be noted, however, that minute irregularities, steps, etc., between the members of the metal rings 111 to 115 and the divided tube members 620 to 625 are left out of consideration here.

[Example of Manufacturing Method]

The catheter 1 according to this embodiment may be manufactured in the following example fashion. First, the catheter tube 11 that includes the tip-flexible part 11A having the foregoing configuration is fabricated.

[Manufacturing Process of Tip-Flexible Part 11A]

Figure 7A:
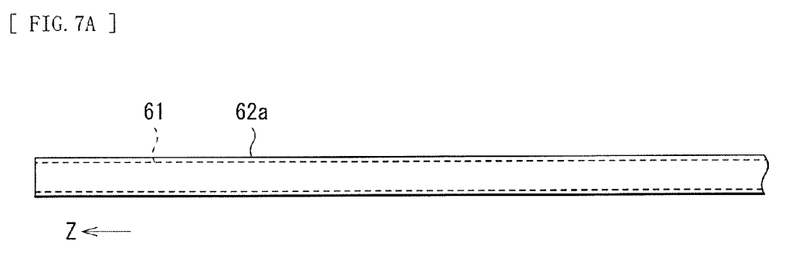
FIG. 7A schematically illustrates an example of a manufacturing process step of the tip-flexible part illustrated in FIGS. 2 to 5.
Figure 7B:
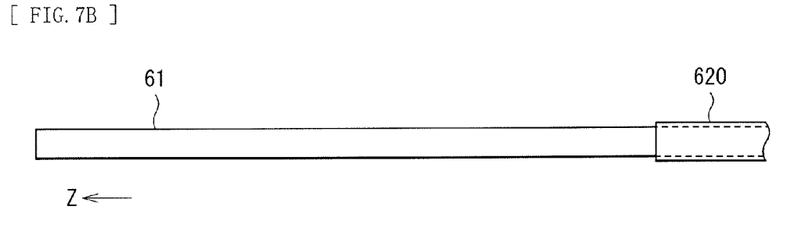
FIG. 7B schematically illustrates an example of a manufacturing process step subsequent to that illustrated in FIG. 7A.
Figure 7C:
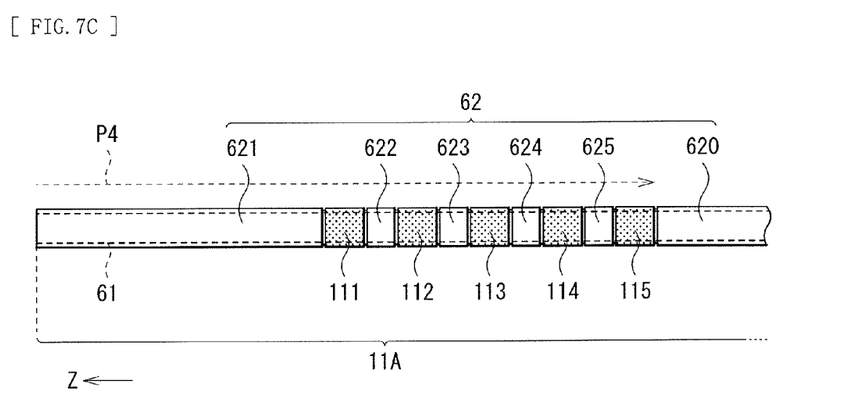
FIG. 7C schematically illustrates an example of a manufacturing process step subsequent to that illustrated in FIG. 7B.

FIGS. 7A to 7C schematically illustrate, in order of process steps, an example of a manufacturing process of the tip-flexible part 11A illustrated in FIGS. 2 to 5.

Referring to FIG. 7A, a tube structure having a multilayer structure, i.e., a two-layer structure, that includes the first tube 61 located on the inner circumference side and a single second tube 62a located on the outer circumference side may be formed first in this example of the manufacturing process as illustrated in FIG. 7A.

Thereafter, a tip of the second tube 62a located on the outer circumference side of the tube structure may be removed by means of a predetermined tool as illustrated by way of example in FIG. 7B. In other words, a part of the tube structure excluding a region that eventually serves as the divided tube member 620 may be removed by means of the predetermined tool. This forms a structure in which the first tube 61 is stripped and thus exposed to the outside in a region in which the metal rings 111 to 115 and the divided tube members 621 to 625 are to be disposed. On this occasion, a certain region of a part of the first tube extending from a tip end to a base end may also be removed by means of a tool such as a graver to thereby form the opening S that may have, for example, the slit shape as described previously. The certain region is, in other words, the region in which the metal rings 111 to 115 and the divided tube members 621 to 625 are to be disposed.

Thereafter, each of the members described previously may be fitted on the outer circumferential surface of the first tube 61 from the tip end to the base end, i.e., toward the divided tube member 620 of the first tube 61, in the following fashion as denoted by arrow P4 of FIG. 7C. Namely, the metal ring 115, the divided tube member 625, the metal ring 114, the divided tube member 624, the metal ring 113, the divided tube member 623, the metal ring 112, the divided tube member 622, the metal ring 111, and the divided tube member 621 each having the foregoing configuration may be fitted sequentially in this order on the outer circumferential surface of the first tube 61 as illustrated in FIG. 7C.

Note that the temperature sensors 51 to 55 and tips of the respective conduction wires L1 to L5 may be respectively coupled in advance to the metal rings 111 to 115 in an individual fashion. Accordingly, upon fitting the metal rings 111 to 115 in the foregoing fashion, base ends of the respective conduction wires L1 to L5 may be first inserted into the lumen 61A of the first tube 61 to draw out those base ends from the base end of the catheter tube 11. Thereafter, each of the metal rings 111 to 115 may be moved from the tip end of the first tube 61 to the base end of the first tube 61 while pulling each of the drawn-out conduction wires L1 to L5 toward the base end side. It is to be noted that the parts at which the temperature sensors 51 to 55 and the conduction wires L1 to L5 are respectively coupled to the metal rings 111 to 115 each may be welded by means of the spot welding as described previously, meaning that welded parts may be raised on the inner circumferential surfaces of the respective metal rings 111 to 115. In this embodiment, however, the first tube 61, i.e., the lumen 61A, may have the slit-shaped opening S from the tip end thereof as described previously, preventing the welded parts from acting as obstacles upon the fitting and allowing the welded parts to be moved in the axial direction of the first tube 61. Hence, it is possible to so dispose the metal rings 111 to 115 as to be fitted on the outer circumference of the first tube 61 even when inner diameters of the respective metal rings 111 to 115 are each similar in value as the outer diameter of the first tube 61.

Thereafter, the tip 110 having the foregoing configuration may be attached to most distal ends of the thus-obtained respective first and second tubes 61 and 62, and each of the operating wires 40a and 40b having the foregoing configurations may be disposed inside the first tube 61. Note that the tip ends of the respective operating wires 40a and 40b may be fixed in advance around the inside of the tip 110 by means of, for example, the anchor and the solder. Accordingly, the base ends of the respective operating wires 40a and 40b may be led to the base end of the catheter tube 11, and the tip 110 may be attached to the most distal ends of the respective first and second tubes 61 and 62. This thus completes the tip-flexible part 11A illustrated in FIGS. 2 to 5. Further, the thus-completed tip-flexible part 11A and other base end parts described previously may be coupled together, whereby the catheter tube 11 illustrated in FIGS. 1 and 2 is obtained.

[Attachment Process of Handle 12]

Thereafter, the handle 12 having the foregoing configuration may be attached to the base end of the catheter tube 11 that includes the thus-manufactured tip-flexible part 11A. On this occasion, the base ends of the respective operating wires 40a and 40b and the base ends of the respective conduction wires L1 to L5 each may be so extended as to be led from the inside of the catheter tube 11 to the inside of the handle 12. The base ends of the respective operating wires 40a and 40b each may also be fixed by the unillustrated fastener inside the handle 12. The foregoing completes the catheter 1 illustrated in FIGS. 1 to 6.

[Workings and Effects]

[A. Basic Operation]

The catheter 1 may measure information on the internal temperature of a hollow organ inside the body, such as the esophagus, of a patient when being used for a medical treatment of arrhythmia, etc., of the patient, e.g., when being used for surgical ablation of the left atrium. Examples of the ablation performed upon the medical treatment may include a high-temperature ablation, i.e., a method that performs heating, that uses a high frequency current and a low-temperature ablation, i.e., a method that performs cooling, that uses liquid nitrous oxide, liquid nitrogen, etc.

Figure 8:
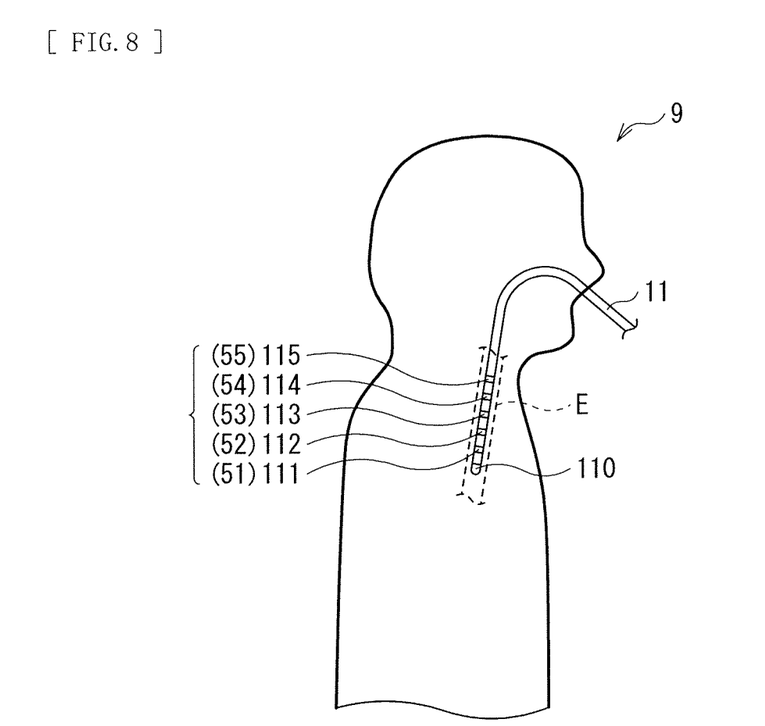
FIG. 8 schematically illustrates an example of a way in which the catheter according to an embodiment is used.

As schematically illustrated in FIG. 8, the catheter tube 11 of the catheter 1 is inserted from the tip, i.e., from the tip-flexible part 11A, of the catheter tube 11 into the esophagus E of a patient 9 through, for example, the nose of the patient 9 by means of a transnasal approach upon performing the measurement of the internal temperature. On this occasion, a shape near the tip, i.e., the tip-flexible part 11A, of the inserted catheter tube 11 may be varied in two directions in response to the rotary operation of the rotary plate 41 performed by the operator of the catheter 1.

More specifically, for example, the operator may grab the handle 12 with his/her one hand and operate the knob 41a with its fingers to rotate the rotary plate 41 in a direction denoted by the arrow d1a of FIG. 1, i.e., in a clockwise direction. This pulls the foregoing operating wire 40*a* toward the base end within the catheter tube 11, thereby causing the region near the tip of the catheter tube 11 to be curved or "deflected" in a direction denoted by the arrow d2*a* of FIG. 1.

Further, for example, the operator may operate the knob 41*b* to rotate the rotary plate 41 in a direction denoted by the arrow d1*b* of FIG. 1, i.e., in a counterclockwise direction. This pulls the foregoing operating wire 40*b* toward the base end within the catheter tube 11, thereby causing the region near the tip of the catheter tube 11 to be curved in a direction denoted by the arrow d2*b* of FIG. 1.

Performing the rotary operation of the rotary plate 41 by the operator in this way makes it possible to swing and deflect the catheter tube 11. Further, rotating the handle body 121 about an axis in an X-Y plane makes it possible to set an orientation of the region near the tip of the catheter tube 11 freely in a curving direction while the catheter tube 11 is inserted in the body, such as the esophagus E, of the patient 9. The catheter 1 is thus provided with the deflection mechanism for the deflection of the tip-flexible part 11A, allowing for the insertion of the catheter tube 11 while varying a shape of the region near the tip, i.e., the tip-flexible part 11A, of the catheter tube 11. Accordingly, it is possible to make the catheter tube 11 pass through the complex-structured nasal cavity smoothly and insert the catheter tube 11 to the esophagus easily.

The tip-flexible part 11A of the catheter tube 11 includes the five metal rings 111 to 115 serving as the temperature measuring metal rings and the five temperature sensors 51 to 55 electrically coupled to the metal rings 111 to 115 in an individual fashion respectively. Utilizing those metals rings and temperature sensors allows for measurement or monitoring of the information on the internal temperature of the esophagus E. Note that the metal ring 111 and the metal ring 115 are so disposed as to respectively measure the lower side and the upper side of the esophagus when the catheter tube 11 of the catheter 1 is inserted, from the tip of the catheter tube 11, into the esophagus E of the patient 9. The lower side and the upper side may be, in other words, the stomach side and the oral cavity side, respectively.

By monitoring the internal temperature of the esophagus E of the patient 9 by means of the catheter 1, it is possible to avoid a possibility that the esophagus E is damaged upon, for example, the foregoing surgical ablation of the left atrium. More specifically, when performing ablation of a site such as the posterior wall of the left atrium of the heart by means of an ablation catheter, i.e., upon the surgical ablation of the left atrium, the esophagus located in the vicinity of the posterior wall of the left atrium may typically be heated or cooled as well, leading to a possible damage of the esophagus. Monitoring the internal temperature of the esophagus E in this way makes it possible to take a precaution and thus to avoid the possibility of the damage.

[B. Workings of Tip-Flexible Part 11A]

The catheter 1 according to this embodiment includes the metal rings 111 to 115 each having the foregoing thick structure. More specifically, the rate of the thickness of each of the metal rings 111 to 115 to the outer diameter of each of the metal rings 111 to 115 is 7.5% or greater. This makes it possible to achieve the following example advantages.

First, the existing thin-structured metal ring described previously involves immediate dissipation of heat having transferred thereto to surrounding tissues, meaning that the internal temperature of a site such as the esophagus E having been subjected to the heating or the cooling fails to be transmitted to the temperature sensors accordingly. For example, this leads to inconsistency in temperature to be detected between a case where the connection part, at which the temperature sensor and the metal ring are coupled together, is located at a part of the esophagus E in proximity to an ablation-performed site of the heart and a case where the connection part is located at a region that is away from the part of the esophagus E in proximity to the ablation-performed site of the heart. In other words, this leads to a large variation in the temperature to be detected depending on which part of, for example, the esophagus E the connection part of the temperature sensor and the metal ring is located, possibly decreasing an accuracy of the measurement upon measuring the internal temperature of, for example, the esophagus E accordingly.

In contrast, the metal rings 111 to 115 according to this embodiment each have the foregoing thick structure. Thus, a rate at which the heat having transferred to the metal rings 111 to 115 dissipates to the surrounding tissues becomes small. This allows for detection of a temperature that is similar to that of the case where the connection parts, at which the temperature sensors 51 to 55 and the corresponding metal rings 111 to 115 are coupled together, are located at the part of the esophagus E in proximity to the ablation-performed site of the heart even when the connection parts are located at the region away from the part of the esophagus E in proximity to the ablation-performed site of the heart. In other words, this makes it possible to measure the internal temperature of, for example, the esophagus E regardless of which part of, for example, the esophagus E the connection parts of the temperature sensors 51 to 55 and the metal rings 111 to 115 are located. Hence, it is possible to increase the accuracy of the measurement upon measuring the internal temperature of, for example, the esophagus E as compared with the existing thin-structured metal ring, owing to the accurate transmission, to the temperature sensors 51 to 55, of the internal temperature of a site such as the esophagus E having been subjected to the heating or the cooling. Accordingly, it is possible to know a change in the temperature of the site such as the esophagus E resulting from the ablation accurately, and to avoid the possibility of the damage of the site such as the esophagus E by taking the precaution before, for example, the esophagus E is damaged.

Note that the thick-structured metal rings 111 to 115 may involve difficulties in employing an example method that causes the metal rings to be embedded into the outer circumferential surface of the second tube upon forming the tip-flexible part 11A of the catheter tube 11. The second tube is, in other words, an outer tube, and serves as a single structural body. For example, in the case of the thick-structured metal rings 111 to 115, it is difficult to employ a method in which the metal rings are struck from the outside to embed those metal rings into the outer circumferential surface of the second tube.

To address this, in this embodiment, the members described previously are so disposed in the tip-flexible part 11A of the catheter tube 11 as to be fitted on the outer circumferential surface of the first tube 61 as illustrated by way of example in FIGS. 2, 3, and 5. In other words, the metal rings 111 to 115 electrically coupled to the temperature sensors 51 to 55, respectively, and the divided tube members 620 to 625 structuring the second tube 62 are so disposed as to be fitted on the outer circumferential surface of the first tube 61 side by side in the axial direction, i.e., the Z-axis direction, of the catheter tube 11. This makes it easier to form the tip-flexible part 11A even when the metal rings 111 to 115 are made thick as described above. Further, the divided tube members 620 to 625 and the metal rings 111 to 115 are formed by disposing them by means of fitting, making it possible to easily vary the shapes of the respective outer circumferential surfaces of the divided tube members 620 to 625 and the metal rings 111 to 115 simply by changing the outer diameter of each of the divided tube members 620 to 625 and the outer diameter of each of the metal rings 111 to 115. Thus, as described later in greater detail, the formation of the outer circumferential surfaces are easy even when the outer circumferential surfaces of the respective metal rings 111 to 115 and divided tube members 620 to 625 are to be formed flat in the axial direction, i.e., the Z-axis direction, thereof.

In particular, in this embodiment, the five metal rings 111 to 115 are so disposed as to be fitted side by side in the axial direction of the catheter tube 11 with the four divided tube members 622, 623, 624, and 625 interposed in between as illustrated by way of example in FIGS. 2, 3, and 5, forming the side-by-side arrangement structure. In other words, the plurality of metal rings 111 to 115 and the plurality of divided tube members 620 to 625 may be disposed alternately. The plurality of metal rings 111 to 115 are thus so disposed as to be fitted side by side at a predetermined interval, making it possible to expand a range of measurement upon measuring the internal temperature of a site such as the esophagus E and thereby to improve convenience upon measuring the temperature.

Further, the metal rings 111 to 115 and the divided tube members 621 to 625 may be so configured as described below as to form the foregoing side-by-side arrangement structure as denoted, for example, by the arrows P1 and P2 of FIG. 5, the arrow P3 of FIG. 6, and the arrow P4 of FIG. 7C. Namely, those members are fitted on the outer circumferential surface of the first tube 61 sequentially in the axial direction, i.e., the Z-axis direction, of the tip-flexible part 11A such that the foregoing side-by-side arrangement structure is formed. Those members are so disposed as to be fitted sequentially, making it possible to form the tip-flexible part 11A more easily.

Note that, owing to the structure of the tip-flexible part 11A in which the members are fitted, a negative impact on the body is small or almost zero in the highly-unlikely event of detachment of the divided tube members 621 to 625 and the metal rings 111 to 115 inside the esophagus F or other sites unlike a case of the blood vessel, etc.

In addition, the tip-flexible part 11A according to this embodiment may have the opening S as illustrated by way of example in FIGS. 3 to 6. The opening S may be formed to allow for the individual electrical coupling of the temperature sensors 51 to 55 and the metal rings 111 to 115. This facilitates the individual electrical coupling of the metal rings 111 to 115 and the temperature sensors 51 to 55 through the opening S, making it possible to form the tip-flexible part 11A more easily.

The opening S may be formed in a region, of the first tube 61, in which the metal rings 111 to 115 and the divided tube members 621 to 625 are disposed as illustrated by way of example in FIGS. 3 to 6. More specifically, the opening S may be formed in a shape of a slit from the tip end of the first tube 61 in the axial direction, i.e., the Z-axis direction, of the tip-flexible part 11A as illustrated by way of example in FIG. 5. In other words, the opening S may be formed in a single, continuous rectangular shape. This makes it easier to form the opening S on the first tube 61, which means that a process of removing the first tube 61 by means of the previously-described method is facilitated. Thus, it is possible to form the tip-flexible part 11A even more easily. Further, forming the opening S from the tip end of the first tube 61 makes it easier to so dispose the metal rings 111 to 115 as to be fitted on the outer circumferential surface of the first tube 61.

Further, in the tip-flexible part 11A, the outer circumferential surfaces of the foregoing respective metal rings 111 to 115 and divided tube members 620 to 625 each may form a flat shape in the axial direction, i.e., the Z-axis direction, thereof as illustrated by way of example in FIGS. 2, 3, and 5. Forming those outer circumferential surfaces into the flat shape in the axial direction makes it possible to achieve the following example advantages according to this embodiment, as compared with an exemplary comparative example in which either of those outer circumferential surfaces is formed in a non-flat shape as described below.

An advantage is that a risk of damaging the inside, or the medial wall, of a site such as the nasal cavity and the esophagus E is suppressed, making it possible to reduce a burden imposed on the patient 9. Another advantage is that the metal rings 111 to 115 come into "surface contact" with the medial wall of a site such as the esophagus E upon measuring the internal temperature of the site such as the esophagus E, making it possible to increase responsiveness, especially the temporal responsiveness, to a change in the temperature upon the measurement and thereby to increase an accuracy of the measurement. Yet another advantage is that forming the outer circumferential surfaces into the flat shape in the axial direction makes it possible to decrease a diameter of the catheter tube 11, i.e., the tip-flexible part 11A.

Figure 9:
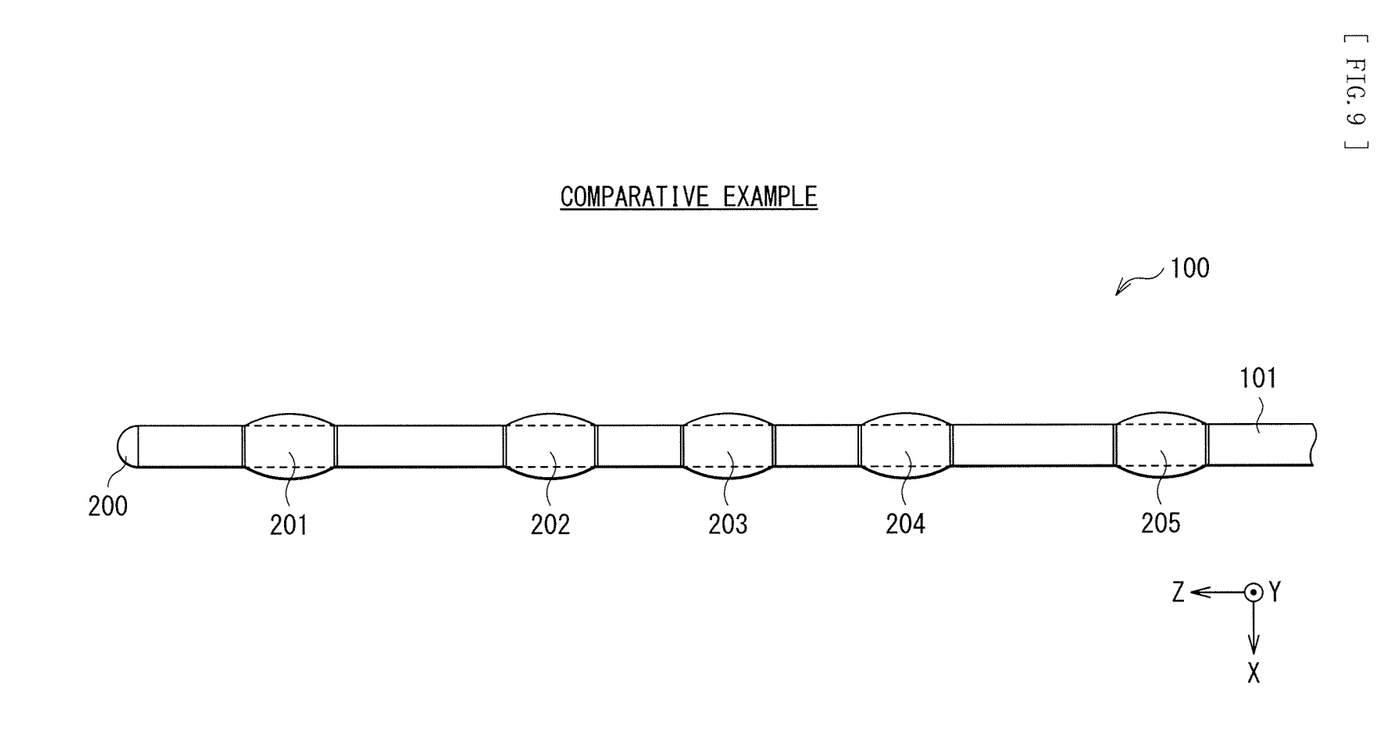
FIG. 9 schematically illustrates a configuration of a part of a catheter according to a comparative example.

FIG. 9 schematically illustrates a configuration, on the Z-X plane, of a region near a tip of a catheter tube 101 of a catheter according to a comparative example. More specifically, FIG. 9 schematically illustrates a configuration, on the Z-X plane, of a tip-flexible part of the catheter tube 101 of a catheter 100 according to the comparative example. The catheter tube 101 according to the comparative example includes a tip 200 attached at a tip end of the catheter tube 101, and five metal rings 201, 202, 203, 204, and 205 that are disposed at a predetermined interval in the tip-flexible part of the catheter tube 101. Note that, unlike the metal rings 111 to 115 according to this embodiment, the metal rings 201 to 205 according to the comparative example form a configuration in which each of the metal rings 201 to 205 is simply placed on or covers an outer circumferential surface, i.e., the surroundings, of the catheter tube 101.

Further, the metal rings 201 to 205 of the catheter tube 101 have their respective outer circumferential surfaces that are non-flat in an axial direction, i.e., the Z-axis direction, of the catheter tube 101 as illustrated in FIG. 9. More specifically, those outer circumferential surfaces each have a bulged shape that protrudes outwardly. Causing each of the outer circumferential surfaces to be non-flat or have the bulged shape brings the following example disadvantages to the comparative example as compared with this embodiment.

A disadvantage is that the bulged shape increases the risk of damaging the inside, or the medial wall, of a site such as the nasal cavity and the esophagus E, which increases the burden imposed on the patient 9 accordingly. Another disadvantage is that the metal rings 201 to 205 come into "point contact" with the medial wall of a site such as the esophagus E upon measuring the internal temperature of the site such as the esophagus E. This decreases the responsiveness, especially the temporal responsiveness, to a change in the temperature upon the measurement and thereby decreases an accuracy of the measurement as well. Yet another disadvantage is that forming the outer circumferential surfaces into the non-flat shape in the axial direction makes it difficult to decrease a diameter of the catheter tube 101, i.e., the tip-flexible part.

According to this embodiment as thus described, the metal rings 111 to 115 and the divided tube members 621 to 625 are both so disposed in the tip-flexible part 11A of the catheter tube 11 as to be fitted on the outer circumferential surface of the first tube 61 side by side in the axial direction, i.e., the Z-axis direction, of the catheter tube 11. The metal rings 111 to 115 each have the thick structure as described above. Thus, it is possible to make the tip-flexible part 11A easily formable even when the metal rings 111 to 115 are made thick. Hence, it is possible to make the catheter 1 manufacturable in a simplified fashion.

[Modification Examples]

Although the invention has been described with reference to one embodiment, the invention is not limited to the embodiment but may be modified in a wide variety of ways.

For example, shapes, locations, materials, etc., of the respective members described in the foregoing embodiment are non-limiting, and may respectively be any other shape, location, material, etc.

In addition, although the catheter tube 11 has been described with specific reference to the configuration thereof in the foregoing embodiment, it is not necessary for the catheter tube 11 to include all of the components. Alternatively, the catheter tube 11 may be further provided with any other component. In one specific example, the catheter tube 11 may include, as a swinging member, a plate spring provided inside the catheter tube 11 and deformable in a direction of flexure. Factors such as locations, shapes, and the number of metal rings 111 to 115 and the tip 110 of the catheter tube 11 are not limited to those referred to in the foregoing embodiment as well. Further, the number of temperature sensors serving as the temperature measuring metal rings and the number of conduction wires are both not limited to those, i.e., five, described in the foregoing embodiment, and may be adjusted in an example range from one to 20 on an as-needed basis. It is, however, desirable that the number of temperature sensors and the number of conduction wires both be 2 or more, desirably be about four or more, for the reasons described above. In addition, the foregoing embodiment has been described by referring to an example in which no temperature sensor is electrically coupled to the tip 110; however, this is non-limiting and the temperature sensor may also be electrically coupled to the tip 110 to allow the tip 110 to have a function of measuring the temperature as well. Each of the temperature sensors, including the previously-mentioned sensor, is not limited to a configuration described in the foregoing embodiment in which the thermocouple is used, and may utilize other sensors such as a thermistor. The metal rings 111 to 115 and the temperature sensors 51 and 55 do not necessarily have to be electrically coupled. The temperature sensors are not limited to those described in the foregoing embodiment which are directed to measurement of the internal temperature of the hollow organ inside the body such as the esophagus, and may be those directed to measurement of a temperature of any other site. In other words, the temperature sensors may be so configured as to allow the catheter to function as a catheter directed to the measurement of the temperature of any other site.

Further, although the handle 12 including the handle body 121 and the rotary operation part 122 has been described with specific reference to the configuration thereof in the foregoing embodiment, it is not necessary for the handle 12 to include all of the components. Alternatively, the handle 12 may be further provided with any other component.

In addition, a configuration of the shape near the tip of the catheter tube 11 is not limited to that described in the forgoing embodiment. Specifically, the forgoing embodiment has been described with reference to an example of the catheter 1 that is of a type referred to as a "bidirectional type" in which the shape near the tip of the catheter tube 11 is varied in two directions in response to an operation made through the rotary plate 41. The invention, however, is not limited thereto. For example, the invention is applicable to a catheter of a type referred to as a "single direction type" in which the shape near the tip of the catheter tube 11 is varied in one direction in response to an operation made through the rotary plate 41. In this case, only a piece of or a single operating wire may be provided as the previously-described operating wire.

Further, the forgoing embodiment has been described with specific reference to the shape, the location, etc., of the opening S formed on the first tube 61. The shape, the location, etc., of the opening S are, however, not limited to those described in the foregoing embodiment. For example, the opening may have a non-slit shape. Alternatively, a plurality of openings independent of each other may be provided as the opening.

The invention claimed is:

1. A catheter comprising:
   a catheter tube including a tip-flexible part, the tip-flexible part having an inner tube and a plurality of divided tube members, the divided tube members being disposed on outer circumference of the inner tube and independent of each other;
   one or a plurality of metal rings disposed in the tip-flexible part;
   one or a plurality of temperature sensors disposed corresponding to the one or the plurality of metal rings; and
   a handle attached at a base end of the catheter tube,
   a radial thickness of at least one metal ring of the one or the plurality of metal rings being 7.5% or greater of an outer diameter of the at least one metal ring, and
   the one or the plurality of metal rings and the divided tube members both being fitted, in the tip-flexible part, on an outer circumferential surface of the inner tube side by side in an axial direction of the catheter tube such that the one or the plurality of metal rings structurally separate the divided tube members.

2. The catheter according to claim 1, wherein the inner tube has an opening that is formed in the axial direction from a tip end of the inner tube and allows the one or the plurality of metal rings and the one or the plurality of temperature sensors to be electrically coupled to one another.

3. The catheter according to claim 1, wherein the one or the plurality of metal rings and the plurality of divided tube members each include an outer circumferential surface that has a flat shape in the axial direction in the tip-flexible part.

4. The catheter according to claim 1 wherein
   the outer diameter of the one or each of the metal rings is in a range from 1.3 mm to 4.0 mm, and
   the thickness of the one or each of the metal rings is in a range from 0.15 mm to 0.50 mm.

5. The catheter according to claim 1, further comprising a deflection mechanism that includes the handle and deflects the tip-flexible part.

6. The catheter according to claim 1, wherein the catheter comprises a temperature-measuring catheter.

* * * * *